(12) United States Patent
Karim et al.

(10) Patent No.: US 9,381,499 B2
(45) Date of Patent: Jul. 5, 2016

(54) CARBON SUPPORTED COBALT AND MOLYBDENUM CATALYST

(75) Inventors: Khalid Karim, Riyadh (SA); Graham Hutchings, Ross-on-Wye (GB); Sarwat Iqbal, South Glamorgan (GB)

(73) Assignee: Saudi Basic Industries Corporation, Riyadh (SA)

( * ) Notice: Subject to any disclaimer, the term of this patent is extended or adjusted under 35 U.S.C. 154(b) by 10 days.

(21) Appl. No.: 14/006,199

(22) PCT Filed: Apr. 19, 2012

(86) PCT No.: PCT/EP2012/001699
§ 371 (c)(1),
(2), (4) Date: Jan. 31, 2014

(87) PCT Pub. No.: WO2012/143131
PCT Pub. Date: Oct. 26, 2012

(65) Prior Publication Data
US 2014/0135411 A1    May 15, 2014

(30) Foreign Application Priority Data

Apr. 19, 2011   (EP) .................................... 11003260

(51) Int. Cl.
| B01J 21/18 | (2006.01) |
| B01J 23/882 | (2006.01) |
| B01J 23/887 | (2006.01) |
| C07C 29/156 | (2006.01) |
| B01J 37/03 | (2006.01) |
| B01J 35/10 | (2006.01) |
| B01J 37/18 | (2006.01) |
| B01J 35/00 | (2006.01) |

(52) U.S. Cl.
CPC ............... B01J 23/882 (2013.01); B01J 21/18 (2013.01); B01J 23/8872 (2013.01); B01J 35/1019 (2013.01); B01J 35/1023 (2013.01); B01J 37/035 (2013.01); C07C 29/156 (2013.01); B01J 35/002 (2013.01); B01J 37/18 (2013.01); C10G 2300/4018 (2013.01); Y02P 20/52 (2015.11)

(58) Field of Classification Search
CPC ...... B01J 21/18; B01J 35/002; B01J 35/1023; B01J 35/1019; B01J 37/035; B01J 23/882; C07C 31/02; C07C 29/156
USPC .................................................. 502/183, 185
See application file for complete search history.

(56) References Cited

U.S. PATENT DOCUMENTS

| 4,177,203 A | 12/1979 | Kolbel et al. |
| 4,752,622 A | 6/1988 | Stevens |
| 4,882,360 A | 11/1989 | Stevens |
| 5,780,381 A | 7/1998 | Wilson et al. |
| 7,375,055 B2 | 5/2008 | Van Berge et al. |
| 7,396,798 B2 | 7/2008 | Ma et al. |
| 2014/0142206 A1 | 5/2014 | Karim et al. |

FOREIGN PATENT DOCUMENTS

| CN | 1631527 A | 6/2005 |
| CN | 101664682 A | 3/2010 |
| CN | 101733135 A | 6/2010 |
| EP | 0119609 A1 | 9/1984 |
| EP | 0172431 A2 | 2/1986 |
| JP | H05-135772 A | 6/1993 |
| JP | 2011-029171 A | 2/2011 |
| WO | WO-03/041860 A2 | 5/2003 |
| WO | WO-03/076074 A1 | 9/2003 |
| WO | WO-2009/032982 A2 | 3/2009 |
| WO | WO-2010/002618 A1 | 1/2010 |
| WO | WO-2010/098668 A2 | 9/2010 |
| WO | WO 2011/003884 A1 | 1/2011 |
| WO | WO-2012/041860 A1 | 4/2012 |
| WO | WO 2012/078277 A1 * | 6/2012 |
| WO | WO-2012/143131 A1 | 10/2012 |
| WO | WO-2013/007345 A1 | 1/2013 |

OTHER PUBLICATIONS

Bao J, et al. (2003) A highly active K—Co—Mo/C catalyst for mixed alcohol synthesis from CO + H2. Chemical Communications, 9(6): 746-747.
Fujimoto K, et al. (1985) Synthesis of C1-C7 alcohols from synthesis gas with supported cobalt catalysts. Applied Catalysis, 13(2): 289-293.
Li X, et al. (1998) Higher alcohols from synthesis gas using carbon-supported doped molybdenum-based cataylsts. Industrial Engineering Chemistry Research, 37(10): 3853-3863.
International Preliminary Report on Patentability issued by the International Bureau on Jan. 14, 2014 for PCT/EP2012/002711 filed on Jun. 28, 2012 and published as WO 2013/007345 on Jan. 17, 2013 (Applicants—Saudi Basic Industries Corporation, et al.; Inventors—Karim, et al.) (7 pages).
International Search Report mailed by the International Bureau on Oct. 31, 2012 for PCT/EP2012/002711 filed on Jun. 28, 2012 and published as WO 2013/007345 on Jan. 17, 2013 (Applicants—Saudi Basic Industries Corporation, et al.; Inventors—Karim, et al.) (4 pages).

(Continued)

Primary Examiner — Jafar Parsa
(74) Attorney, Agent, or Firm — Ballard Spahr LLP

(57) ABSTRACT

The present invention relates to a catalyst composition comprising cobalt molybdenum and optionally one or more elements selected from the group consisting of alkali metals and alkaline earth metals on a carbon support wherein said cobalt and molybdenum are in their metallic form. It was surprisingly found that the selectivity for alcohols can be increased by using the carbon supported cobalt molybdenum catalyst as described herein in a process for producing alcohols from a feed stream comprising hydrogen and carbon monoxide. Furthermore, it was found that the catalyst of the present invention has a decreased selectivity for CO2 and can be operated at relatively low temperature when compared to conventional catalysts. Moreover, a method for preparing the carbon supported cobalt molybdenum catalyst composition and a process for producing alcohols using said carbon supported cobalt molybdenum catalyst composition is provided.

6 Claims, 2 Drawing Sheets

(56) References Cited

OTHER PUBLICATIONS

Written Opinion mailed by the International Bureau on Oct. 31, 2012 for PCT/EP2012/002711 filed on Jun. 28, 2012 and published as WO 2013/007345 on Jan. 17, 2013 (Applicants—Saudi Basic Industries Corporation, et al.; Inventors—Karim, et al.) (6 pages).

Extended European Search Report issued on Dec. 23, 2011 for EP 11075164.1 (Applicants—Saudi Basic Industries Corporation, et al.; Inventors—Karim, et al.) (7 pages).

Preliminary Amendment filed Nov. 25, 2013 for U.S. Appl. No. 14/122,181, filed Feb. 4, 2014 and published as U.S. 2014/0142206 on May 22, 2014 (Applicants—Saudi Basic Industries Corporation, et al.; Inventors—Karim, et al.) (6 pages).

Auer (1998) Carbons as supports for industrial precious metal catalysts. Applied Catalysis A: General, 173: 259-271.

Commereuc (1980) Catalytic synthesis of low molecular weight olefins from CO ; and H2 with Fe (CO)5, FE3(CO)12, and [HFe3(CO)11]—supported on inorganic oxides. J. Chem. Soc., Chem. Commun.: 154-155.

Dry (2004) Chapter 3—Chemical concepts used for engineering purposes. Stud. Surf. Sci. Catal, 152: 196-257.

Mirzaei, et al. (2009) Fischer-Tropsch Synthesis over Iron Manganese Catalysts: Effect of Preparation and Operating Conditions on Catalyst Performance. Adv. Phys. Chem, 2009: 1-12.

Okuhara (1981) Synthesis of light olefins from CO and H2 over highly dispersed Ru/K—Al2O3 derived from Ru3(Co)12. J. Chem. Soc., Chem. Commun., 1981(21): 1114-1115.

International Preliminary Report on Patentability issued by the International Bureau on Oct. 22, 2013 for PCT/EP2012/001699 filed Apr. 19, 2012 and published as WO 2012/143131 on Oct. 26, 2012 (Applicants—Saudi Basic Industries Corporation, et al.; Inventors—Karim, et al.) (5 pages).

International Search Report mailed by the International Bureau on Jul. 17, 2013 for PCT/EP2012/001699 filed Apr. 19, 2012 and published as WO 2012/143131 on Oct. 26, 2012 (Applicants—Saudi Basic Industries Corporation, et al.; Inventors—Karim, et al.) (2 pages).

Written Opinion mailed by the International Bureau on Jul. 17, 2013 for PCT/EP2012/001699 filed Apr. 19, 2012 and published as WO 2012/143131 on Oct. 26, 2012 (Applicants—Saudi Basic Industries Corporation, et al.; Inventors—Karim, et al.) (4 pages).

Knuniants, et al., Soviet Chemical Encyclopedia, vol. 2, (1990) (pp. 338-339).

Matos, et al., "Activated carbon supported Ni—Mo: effects of pretreatment and composition on catalyst reducibility and on ethylene conversion", Applied Catalysis A: General 152 (1997) (pp. 27-42).

* cited by examiner

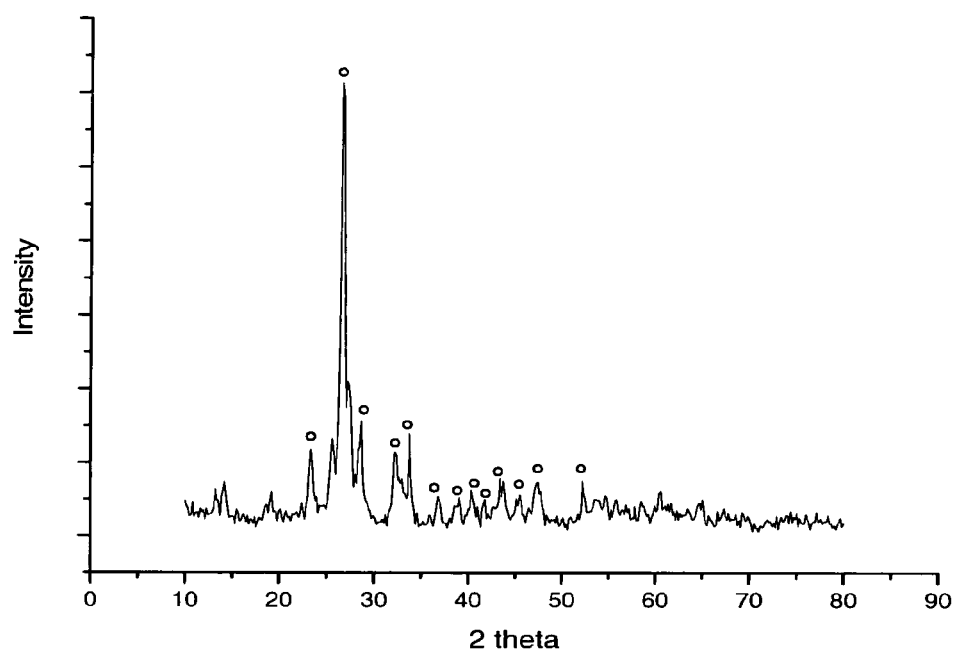
Figure 1. XRD pattern of catalyst composition prepared in Example 2

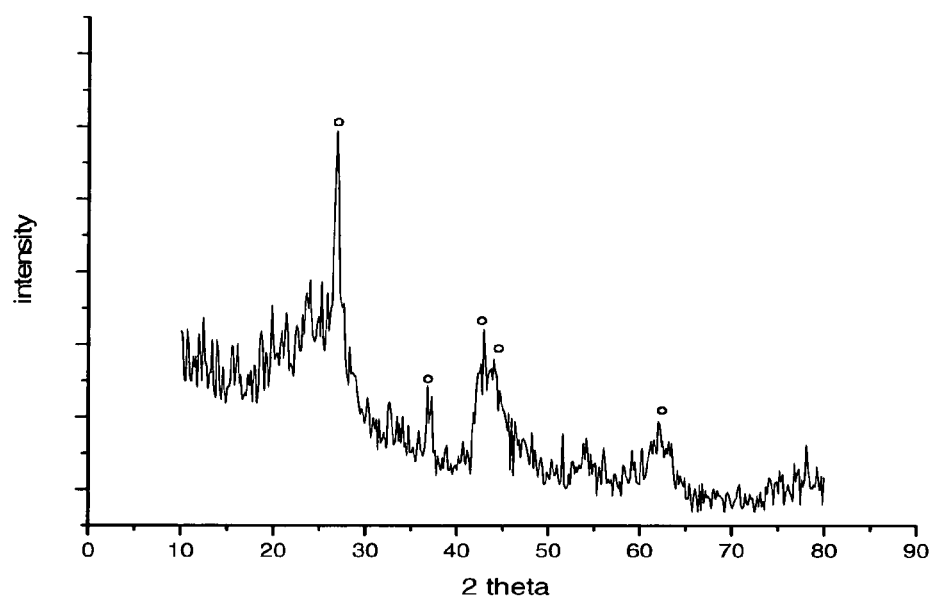
Figure 2. XRD pattern of catalyst composition prepared in Example 3

CARBON SUPPORTED COBALT AND MOLYBDENUM CATALYST

CROSS REFERENCE TO RELATED APPLICATIONS

The present application is a National Phase Application of International Application No. PCT/EP2012/001699, filed Apr. 19, 2012, which claims priority to European Patent Application No. 11003260.4, filed Apr. 19, 2011, which applications are incorporated herein fully by this reference.

The present invention relates to a catalyst composition comprising cobalt molybdenum and optionally one or more elements selected from the group consisting of alkali metals and alkaline earth metals on a carbon support wherein said cobalt and molybdenum are in their metallic form. It was surprisingly found that the selectivity for alcohols can be increased by using the carbon supported cobalt molybdenum catalyst as described herein in a process for producing alcohols from a feed stream comprising hydrogen and carbon monoxide. Furthermore, it was found that the catalyst of the present invention has a decreased selectivity for $CO_2$ and can be operated at relatively low temperature when compared to conventional catalysts. Moreover, a method for preparing the carbon supported cobalt molybdenum catalyst composition and a process for producing alcohols using said carbon supported cobalt molybdenum catalyst composition is provided.

Gaseous mixtures comprising hydrogen ($H_2$) and carbon monoxide (CO) can be converted into a hydrocarbon product stream by a catalytic process known as Fischer-Tropsch synthesis (F-T synthesis). The most common catalysts useful in F-T synthesis ("F-T catalysts") are based on Fe and/or Co, although Ni- and Ru-based catalysts have also been described (see e.g. U.S. Pat. No. 4,177,203; Commereuc (1980) J. Chem. Soc., Chem. Commun. 154-155; Okuhara (1981) J. Chem. Soc., Chem. Commun. 1114-1115). Generally, Ni-based catalysts are relatively more selective for producing methane whereas Co-, Fe- and Ru-based catalysts are more selective for hydrocarbons having at least two carbon atoms (C2+ hydrocarbons). Moreover, the selectivity for C2+ hydrocarbons can be increased by decreasing the $H_2$:CO ratio, decreasing the reaction temperature and decreasing the reactor pressure.

It has been previously described that alcohols may be produced by F-T synthesis using a catalyst composition having as a first component molybdenum in free or combined form, as a second component a promoter of an alkali or alkaline earth element in free or combined form and as a third component cobalt in free or combined form (see EP 0 172 431 A2). Preferably, the first and third component is present as the sulphide. The catalyst of EP 0 172 431 A2 may further comprise a support, wherein carbon supports are preferred.

WO 2010/002618 A1 describes a catalyst comprising elemental molybdenum, cobalt or their alloy and an alkali or alkaline earth metal and/or hybrids thereof, in an elemental ratio of about 2-1:1:0.08-0.30, carried on a porous, inert particularized material and the use of said catalyst in a process for making alcohols by passing syngas through a reactor containing said catalyst. The preferred support used for the catalyst according to WO 2010/002618 A1 is alumina, wherein the catalyst has a surface area of about 210 $m^2/g$.

A major drawback of conventional catalysts for producing alcohols by F-T synthesis is that the selectivity of the process for alcohols is relatively low.

It was an object of the present invention to provide an improved catalyst suitable for producing alcohols from a syngas mixture comprising hydrogen and carbon monoxide.

The solution to the above problem is achieved by providing the embodiments as described herein below and as characterized in the claims. Accordingly, the present invention provides a catalyst composition comprising cobalt (Co); and molybdenum (Mo) on an activated carbon support (C) wherein the relative molar ratios of the elements comprised in said composition are represented by the formula:

$$Co_aMo_bM_cC$$

wherein:
M is one or more elements selected from the group consisting of alkali metal and alkaline earth metal;
a is 1E-3-0.3;
b is 1E-3-0.9
c is 0-1E-2; and
wherein said Co and Mo are in their metallic form and wherein the catalyst composition has a BET surface area of at least 320 $m^2/g$.

In the context of the present invention, it was surprisingly found that both the CO conversion and the selectivity for alcohols can be increased by using the activated carbon supported cobalt molybdenum catalyst as described herein in a process for producing alcohols from a feedstream comprising hydrogen and carbon monoxide. Furthermore, it was found that the catalyst of the present invention has a decreased selectivity for $CO_2$ and can be operated at relatively low temperature in a process for producing alcohols from a syngas mixture comprising hydrogen and carbon monoxide when compared to conventional catalysts. It was found that particularly the specific combination of the metallic Co and Mo and the selection of a carbon supported catalyst composition having a BET surface area of at least 320 $m^2/g$ leads to the advantageous effects of the present invention.

The present invention accordingly relates to an activated carbon supported cobalt and molybdenum catalyst composition wherein the comprised Co and Mo are in their metallic form. This means that at least 90 mole-%, more preferably at least 95 mole-% and most preferably at least 99 mole-% of the Co and Mo comprised in the catalyst composition have the oxidation state "zero" (0).

Preferably, the Co and/or Mo comprised in the catalyst composition of the invention are not in sulphide form. This means that the catalyst composition of the present invention has not been sulphided with e.g. $H_2S$ as taught in EP 0 172 431 A2.

Furthermore, it was surprisingly found that a carbon supported catalyst composition has both an improved CO conversion and alcohol selectivity in case the BET surface area of said catalyst composition is at least 320 $m^2$. The surface area of the catalyst composition inter alia depends on the surface area of the activated carbon support particles and the calcination temperature used when preparing the catalyst composition. Preferably, the catalyst composition has a BET surface area of 320-1500 $m^2/g$, more preferably of 320-1200 $m^2/g$, even more preferably of 350-1200, particularly preferably of 350-1000 and most preferably of 350-800 $m^2/g$.

The term "BET surface area" is a standardized measure to indicate the specific surface area of a material which is very well known in the art. Accordingly, the BET surface area as used herein is measured by the standard BET nitrogen test according to ASTM D-3663-03, ASTM International, October 2003.

The amount of Co present in the catalyst composition is determined by the molar ratio of Co in relation to the carbon support C in the catalyst composition. The molar ratio of Co:C is 1E-3-0.3:1 (also depicted as: $Co_aC$ wherein a is 1E-3-0.3:1 or 0.001-0.3:1). This means that the molar ratio of Co:C is between 1E-3:1 (or 0.001:1) and 0.3:1. Most preferably, the molar ratio of Co:C is 1E-2-0.3. It was found that when the catalyst composition comprises too much Co, the catalytic activity shifts towards hydrogenation which decreases catalyst selectivity for oxygenates and increases catalyst selectivity for non-oxygenated hydrocarbons.

The amount of Mo present in the catalyst composition is determined by the molar ratio of Mo in relation to the carbon support C in the catalyst composition. The molar ratio of Mo:C is 1E-3-0.9:1 (also depicted as: $Mo_bC$ wherein b is 1E-3-0.9:1 or 0.001-0.9:1). This means that the molar ratio of Mo:C is between 1E-3:1 (or 0.001:1) and 0.9:1. Most preferably, the molar ratio of Mo:C is 5E-3-0.2. It was found that selectivity of the catalyst for $CO_2$ is increased when the catalyst composition comprises too much Mo. Moreover, it was found that the selectivity of the catalyst for oxygenates decreased when the catalyst comprises too little Mo.

Preferably, the molar ratio of Co:Mo is 1 or more. It was surprisingly found that catalyst selectivity for oxygenates is increased when the molar ratio of Co:Mo is 1 or more. More preferably, the molar ratio of Co:Mo is 1.2-4, even more preferably 1.5-3, particularly preferably 2-2.5 and most preferably 2.1-2.3.

The catalyst composition of the present invention may further comprise one or more elements selected from the group consisting of alkali metal and alkaline earth metal (depicted herein as "M"). Preferably, the one or more alkali metals that may be comprised in the catalyst composition are selected from the group consisting of sodium (Na), potassium (K), rubidium (Rb) and caesium (Cs), more preferably selected from the group consisting of sodium (Na), potassium (K) and caesium (Cs), and most preferably is potassium (K). The one or more alkaline earth metals that may be comprised in the catalyst composition are preferably selected from the group consisting of magnesium (Mg), calcium (Ca), strontium (Sr) and barium (Ba), and more preferably selected from the group consisting of magnesium (Mg) and calcium (Ca).

The amount of M present that may be present in the catalyst composition is determined by the molar ratio of M in relation to the carbon support C in the catalyst composition. The molar ratio of M:C is 0-1E-2 (also depicted as: $M_cC$ wherein c is 0-1E-2:1 or 0-0.01:1). This means that the molar ratio of M:C is between 0 and 1E-2:1 (or 0.01:1). Preferably, the molar ratio of M:C is >0-1E-2. The term ">0" means that M must be present in the catalyst composition. Most preferably, the molar ratio of M:C is 1E-4-1E-2. Without being bound by theory, it is believed that the concentration of alkali and alkaline earth metals can affect the weakening or strengthening of C—O bonds. Accordingly, the presence of an electron-donating species on the catalyst surface may suppress the adsorption of hydrogen because hydrogen itself donates an electron to metal upon adsorption. Furthermore, heat of adsorption of hydrogen may decrease with an increase in alkali metal and/or alkaline earth metal which confirms that addition of M may suppresses adsorption of hydrogen in a certain range. As a result thereof, the catalyst the selectivity to desired products may be enhanced in case a critically required concentration of alkali metal and/or alkaline earth metal is comprised in the catalyst composition.

The catalyst composition of the present invention is preferably formed in regularly sized particles such as conventionally formed catalyst pellets and/or sieved catalyst particles. The catalyst composition of the present invention may comprise further components including but not limited to binders and lubricants. Any inert catalyst binder may be used. Preferably, the binder is selected from the group consisting of bentonite clay, colloidal silica and kaolin. Suitable lubricants are selected from the group consisting of hydrogenated cottonseed oil and hydrogenated soybean oil.

In a further embodiment, the present invention relates to a method for preparing the catalyst composition as described herein, wherein said method comprises the steps of:
(a) preparing a mixture comprising activated carbon support particles having a BET surface area of 700-1500 $m^2/g$ and a solution comprising soluble Co- and Mo-comprising salts;
(b) precipitating the Co and Mo by converting the soluble Co- and Mo-comprising salts into insoluble Co- and Mo-comprising salts, optionally followed by admixing a solution comprising M;
(c) separating the solids from the liquid to obtain the catalyst precursor; and
(d) contacting the catalyst precursor with a reducing agent at a temperature of 300-550° C.

Preferably, the step of contacting the catalyst precursor with a reducing agent comprises the steps of:
(d1) calcining the catalyst precursor in an inert atmosphere to obtain the calcined catalyst precursor; and
(d2) contacting the calcined catalyst precursor with a reducing agent.

Preferably, the activated carbon support particles have a specific surface area of 700-1500 $m^2/g$, more preferably of 800-1200 $m^2/g$, even more preferably of 800-1000 $m^2/g$ and most preferably of 800-900 $m^2/g$. Carbon catalyst support particles are very well known in the art and may be prepared from coals and coal-like materials, petroleum-derived carbons and plant-derived carbons (see Auer (1998) Applied Catal 259-271). Most preferably, the carbon support particles used in the present method is derived from coconut shell carbon and has a specific surface area of 800-900 $m^2/g$.

In the cobalt-molybdenum-solution preparation step (a) as described herein, a solution comprising soluble cobalt- and molybdenum-comprising salts is prepared. The solvent and the obtained solution may be heated to facilitate dissolving of the cobalt- and molybdenum-comprising salts. Preferably, the solvent and the obtained solution is heated to at least 60° C. and up to 95° C. (60-95° C.), most preferably to 75-85° C. The cobalt-molybdenum-solution may be made in any suitable solvent. Suitable solvents are all compounds in which the chosen salts are soluble and which are easy to remove again in the separation step as defined herein. Aqueous solutions, however, are preferred. Most preferably, the solvent is water ($H_2O$).

In the precipitate forming step (b) as described herein, a precipitate is formed by converting the soluble cobalt- and molybdenum-comprising salts into insoluble compounds, e.g. by admixing an alkaline solution as precipitant, preferably under constant agitation. Preferably, the precipitate is formed by admixing a suitable amount of ammonium hydroxide to a cobalt-molybdenum-solution. The amount of alkaline compound present in the alkaline solution is selected so that it is at least sufficient for the stoichiometric reaction with the soluble cobalt- and molybdenum-comprising salts present. Preferably, the amount of alkaline compound present in the alkaline solution is 1-10 times the stoichiometric required amount. Preferably, the ammonium hydroxide is heated to the same temperature as the cobalt-molybdenum-solution. The pH at the end of the precipitation step preferably is at least 8, more preferably at least 9. The temperature of the mixture may be kept constant until the precipitate is formed, preferably under constant agitation. It was surprisingly found that the catalyst selectivity pattern of alcohols depends on the pH of precipitation mixture and the concentration of precipitant.

The pH difference and concentration of the precipitant also affects the morphology of catalyst material.

The method for preparing the catalyst composition according to the present invention also covers a method wherein first a solution comprising a soluble Co-comprising salt is prepared and a Co-comprising precipitate is formed as described herein above wherein subsequently a soluble Mo-comprising salt is dissolved and precipitated. Alternatively, the method for preparing the catalyst composition according to the present invention also covers a method wherein first a solution comprising a soluble Mo-comprising salt is prepared and a Mo-comprising precipitate is formed wherein subsequently a soluble Co-comprising salt is dissolved and precipitated.

Optionally, a solution of a salt comprising one or more elements selected from the group consisting of the alkali metal elements and the alkaline earth metal elements is admixed to the solution comprising the precipitate, preferably under continuous agitation, to form a modified precipitate. The solutions used to modify the precipitate may be made in any suitable solvent. Aqueous solutions, however, are preferred. Most preferably, the solvent is water ($H_2O$).

In the precipitate separation step (c) as described herein, the formed precipitate (i.e. the solid phase of the mixture that is formed after completing the modified precipitate forming step (b)) is separated from the liquid (i.e. the liquid phase of the mixture that is formed after completing the precipitate forming step (b)) using any conventional method which allows the separation of a precipitate from a solvent. Suitable methods include, but are not limited to, filtering, decanting and centrifugation. Subsequently the obtained catalyst precursor may be washed, preferably using the solvent in which the solutions were made, more preferably with water, most preferably with distilled water. The catalyst precursor then may be dried, preferably at 110-120° C. for 4-16 hours.

In the calcining step (d1) as described herein, the catalyst precursor is calcined in an inert atmosphere to form a calcined catalyst precursor. Preferably, the catalyst precursor is calcined at 450-650° C. for 5-10 hrs for 4-24 hours. The skilled person is readily capable of selecting a suitable inert gas to form the inert atmosphere. Preferred inert gases are selected from the group consisting of nitrogen and helium.

After calcination, the calcined catalyst precursor may be formed into pellets using any conventional method. Said pellets may subsequently be sieved to obtain regularly sized particles. Said particles may be sized between 0.65-0.85 mm.

In the reducing step (d) or (d2) as described herein, the calcined catalyst precursor is contacted with a reducing agent. This is to reduce the comprised Co and Mo to its metallic state and results in the formation of metallic Co and Mo as comprised in the catalyst composition as defined herein.

Any suitable reducing agent may be used in the reducing step of this invention. Preferably, the reducing step is performed using a reducing agent in the gas phase. The preferred reducing agent is selected from the group consisting of hydrogen ($H_2$) and carbon monoxide (CO). The reduction can be carried out at ambient temperature or at elevated temperature. Preferably, the reduction is carried out at a temperature of at least 300° C., more preferably of at least 350° C. and up to 550° C., more preferably up to 500° C. Preferably, calcined catalyst precursor is contacted with a reducing agent for at least 14 hrs, more preferably for at least 16 hrs and up to 24 hrs, more preferably up to 20 hrs.

Preferably, the reducing step is performed "in situ". The term "in situ" is well known in the field of chemical engineering and refers to industrial plant operations or procedures that are performed in place. For example, aged catalysts in industrial reactors may be regenerated in place (in situ) without being removed from the reactors; see e.g. WO 03/041860 and WO 03/076074. In the context of the present invention, accordingly, a catalyst composition that is reduced in situ refers to a catalyst composition wherein the reducing step is performed in place, i.e. in the same enclosure that is later present in the process installation in which the catalysed process takes place. In one embodiment, the reducing step as defined herein is performed while the "calcined catalyst precursor" is already present in the catalyst enclosure that is situated in the process installation wherein the catalyst composition is to be employed. In a further embodiment, the reducing step as defined herein is performed while the "calcined catalyst precursor" is already present in the catalyst enclosure which can be directly placed into said process installation.

In a further embodiment of the present invention a catalyst composition obtainable by the herein above described method for preparing a catalyst composition is provided. Accordingly, the present invention relates to a catalyst composition obtainable by the method comprising the steps:
(a) preparing a mixture comprising activated carbon support particles having a BET surface area of 700-1500 $m^2/g$ and a solution comprising soluble Co- and Mo-comprising salts;
(b) precipitating the Co and Mo by converting the soluble Co- and Mo-comprising salts into insoluble Co- and Mo-comprising salts, optionally followed by admixing a solution comprising M;
(c) separating the solids from the liquid to obtain the catalyst precursor; and
(d) contacting the catalyst precursor with a reducing agent at a temperature of 300-550° C.

In a further embodiment, the present invention relates to a process for producing a product stream comprising alcohols comprising contacting the catalyst composition as described herein with a gaseous mixture comprising hydrogen and carbon monoxide (syngas mixture). The product stream comprising alcohols is preferably produced by Fischer-Tropsch synthesis.

The terms "alcohols" is very well known in the art. Accordingly, an "alcohol" relates to any hydrocarbon compound in which a hydroxyl functional group (—OH) is bound to a carbon atom, usually connected to other carbon or hydrogen atoms. Preferred alcohols comprised in the product stream of the present process are C1-C4 alcohols, such as methanol, ethanol, propanol and 1-butanol.

In the context of the present invention, it was surprisingly found that the process for producing alcohols from a feedstream comprising hydrogen and carbon monoxide as described herein has an increased selectivity for alcohols and a decreased selectivity for the undesired by-product $CO_2$. Furthermore, it was found that the process of the present invention can be operated at relatively low temperature which allows a more cost-effective operation.

In the process of the present invention, the catalyst composition is preferably comprised in a fixed bed reactor or a fluidized bed reactor.

Preferably, the syngas mixture has a hydrogen ($H_2$) to carbon monoxide (CO) molar ratio of 0.5-5 (i.e. $H_2$:CO is 1:0.5 to 1:5). Preferably, the syngas mixture has a hydrogen ($H_2$) to carbon monoxide (CO) molar ratio of 1-4 (i.e. $H_2$:CO is 1:1 to 1:4). The term "syngas mixture" as used herein relates to a gaseous mixture substantially consisting of hydrogen ($H_2$) to carbon monoxide (CO). The syngas mixture, which is used as a feed stream to the present process for producing alcohols, may comprise up to 10 mol-% of other components such as $CO_2$ and lower hydrocarbons (lower HC, such as methane). Said other components may be side-products or unconverted products obtained in the process used for producing the syngas mixture. Preferably, the syngas mixture comprises substantially no molecular oxygen ($O_2$). As used herein, the term "syngas mixture comprising substantially no $O_2$" relates to a syngas mixture which comprises such a low amount of $O_2$ so that the comprised $O_2$ does not interfere with the Fischer-Tropsch synthesis reaction. Preferably, the syngas mixture comprises not more than 1 mol-% $O_2$, more preferably not more than 0.5 mol-% $O_2$ and most preferably not more than 0.4 mol-% $O_2$.

The process conditions useful in the process of the present invention can be easily determined by the person skilled in the art; see Dry (2004) Stud. Surf. Sci. Catal 152:197-230 in "Fischer-Tropsch technology" eds. Steynberg and Dry. Accordingly, the Fischer-Tropsch synthesis is performed at a reaction temperature of 150-450° C., preferably of 150-350° C., a space velocity of 400-5000 $h^{-1}$, preferably of 2000 $h^{-1}$ and a pressure of between atmospheric and 20 MPa, preferably a pressure of 1-8 MPa. The catalyst may be stabilized for 80-100 hours at 150-350° C. before actual use.

In this respect, it should be noted that the reaction conditions have a marked effect on the catalytic performance. It has been reported that selectivity on a carbon basis is essentially a function of the probability of chain growth, a; see Dry (2004) loc. cit. Control of the product selectivity is to a large extent determined by the factors that influence the value of α. The main factors are the temperature of the reaction, the gas composition and more specifically the partial pressures of the various gases in contact with catalyst inside the reactor. Overall, by manipulating these factors a high degree of flexibility can be obtained regarding the type of product and the carbon range. An increase in FT-synthesis operating temperature shifts the selectivity profile to lower carbon number products. Desorption of growing surface species is one of the main chain termination steps and since desorption is an endothermic process so a higher temperature should increase the rate of desorption which will result in a shift to lower molecular mass products. Similarly, the higher the CO partial pressure the more is the catalyst surface covered by adsorbed monomers. The lower the coverage by partially hydrogenated CO monomers the higher the probability of chain growth is expected to be; see also Mirzaei et al., Adv. Phys. Chem., 2009, 1-12. Accordingly, the two key steps leading to chain termination are desorption of the chains yielding unsaturated hydrocarbons and hydrogenation of the chains to yield saturated hydrocarbons.

In the context of the present invention, it was surprisingly found that the catalyst of the present invention has an improved activity at relatively low reaction temperatures. Accordingly, the process of the present invention can be very efficiently operated at a reaction temperature of 250° C. which is significantly lower than the optimal reaction temperature of a conventional F-T process for producing alcohols.

In a further embodiment, the present invention relates to a process for producing a product stream comprising alcohols comprising the method for preparing the catalyst composition as described herein and contacting the obtained catalyst composition with a syngas mixture.

In the present invention, the product stream comprising alcohols is preferably produced by Fischer-Tropsch synthesis.

Accordingly, the present invention provides a process for producing a product stream comprising alcohols, preferably by Fischer-Tropsch synthesis, comprising:

(a) preparing a mixture comprising activated carbon support particles having a BET surface area of 700-1500 $m^2/g$ and a solution comprising soluble Co- and Mo-comprising salts;
(b) precipitating the Co and Mo by converting the soluble Co- and Mo-comprising salts into insoluble Co- and Mo-comprising salts, optionally followed by admixing a solution comprising M;
(c) separating the solids from the liquid to obtain the catalyst precursor; and
(d) contacting the catalyst precursor with a reducing agent at a temperature of 300-550° C.

MODE(S) FOR CARRYING OUT THE INVENTION

The present invention will now be more fully described by the following non-limiting Examples.

EXAMPLE 1 (COMPARATIVE)

$CoMoS_2$

A co-precipitated cobalt/molybdenum sulfide is prepared with a Mo/Co atomic ratio of about 2:1. Fifteen grams of $(NH_4)_6Mo_7O_{24}.4H_2O$ (0.085 Moles Mo) is dissolved in 106 $cm^3$ of 22% $(NH_4)_2S$ in water and stirred at 60° C. for one hour to form $(NH_4)_2MoS_4$. A solution of 10.5 grams of $Co(CH_3CO_2)_2$ (0.042 moles Co) in 200 ml of water was prepared. The two solutions were then added simultaneously, drop wise to a stirred solution of 30% aqueous acetic acid in a baffled flask at 50° C. over a one hour period. After stirring for an additional hour the reaction mixture is filtered and the filter cake dried at room temperature and then calcined for one hour at 500° C. in an inert atmosphere such as nitrogen. The calcined Co/Mo Sulfide is ground together with 2.0 g of bentonite clay, 1.0 g of $K_2CO_3$ and 0.4 g of sterotex lubricant in a mortar and pestles and used for catalyst testing.

EXAMPLE 2

$Co_{0.159}Mo_{0.079}C$ 100 ml each of Co and Mo solutions was prepared by dissolving 10.5 g of cobalt acetate $[Co(CH_3CO_2)_2]$ and 15 g of ammonium molybdate tetrahydrate $[(NH_4)_6Mo_7O_{24}.4H_2O]$ in distilled water. Both solutions were premixed and heated to 80° C. The $NH_3$ precipitating solution (200 ml of 11.6M $NH_3$ solution) was also preheated to 80° C. 6.4 g of activated carbon (derived from coconut shell having a BET surface area of 800 $m^2/g$) was added into 100 ml of distilled water in the precipitation vessel. Both reagents (mixed metal salts solutions and $NH_3$ solution) were combined together in the reaction vessel at 80° C. at a combined pumping rate of 6.7 ml/min (3.3 ml/min $NH_3$ solution, 3.3 ml/min metals solution). The reagents were combined in the reaction vessel (80° C.) containing activated carbon in 100 ml of water. The pH was varied from 4.35-8.00. The duration of reaction was 1 h. This solution was immediately filtered through a preheated funnel and washed (using 500 ml of warm distilled water). The precipitates were dried at 110° C. for 16 h followed by calcinations at 500° C. under continuous flow of helium for 24 h. The calcined catalysts were pelleted and sieved (0.65-0.85 mm).

EXAMPLE 3

$Co_{0.159}Mo_{0.079}C$ 100 ml each of Co and Mo solutions was prepared by dissolving 10.5 g of cobalt acetate [$Co(CH_3CO_2)_2$] and 15 g of ammonium molybdate tetrahydrate [$(NH_4)_6Mo_7O_{24}\cdot 4H_2O$] in distilled water. Both solutions were premixed and heated to 80° C. The $NH_3$ precipitating solution (200 ml of 5.6M $NH_3$ solution) was also preheated to 80° C. 6.4 g of activated carbon (derived from coconut shell having a BET surface area of 800 $m^2/g$) was added into 100 ml of distilled water in the precipitation vessel. Both reagents (mixed metal salts solutions and $NH_3$ solution) were combined together in the reaction vessel at 80° C. at a combined pumping rate of 6.7 ml/min (3.3 ml/min $NH_3$ solution, 3.3 ml/min metals solution). The reagents were combined in the reaction vessel (80° C.) containing activated carbon in 100 ml of water. The pH was varied from 4.35-9.00. The duration of reaction was approximately 1 h. This solution was immediately filtered through a preheated funnel and washed (using 500 ml of warm distilled water). The precipitates were dried at 110° C. for 16 h followed by calcinations at 500° C. under continuous flow of helium for 24 h. The calcined catalysts were pelleted and sieved (0.65-0.85 mm).

EXAMPLE 4

$Co_{0.126}Mo_{0.766}C$ 100 ml each of Co and Mo solutions was prepared by dissolving 10.5 g of cobalt acetate [$Co(CH_3CO_2)_2$] and 45.08 g of ammonium molybdate tetrahydrate [$(NH_4)_6Mo_7O_{24}\cdot 4H_2O$] in distilled water. Both solutions were premixed and heated to 80° C. The $NH_3$ precipitating solution (200 ml of 5.6M $NH_3$ solution) was also preheated to 80° C. 4 g of activated carbon (derived from coconut shell having a BET surface area of 800 $m^2/g$) was added into 100 ml of distilled water in the precipitation vessel. Both reagents (mixed metal salts solutions and $NH_3$ solution) were combined together in the reaction vessel at 80° C. at a combined pumping rate of 6.7 ml/min (3.3 ml/min $NH_3$ solution, 3.3 ml/min metals solution). The reagents were combined in the reaction vessel (80° C.) containing activated carbon in 100 ml of water. The pH was varied from 4.35-9.00. The duration of reaction was approximately 1 h. This solution was immediately filtered through a preheated funnel and washed (using 500 ml of warm distilled water). The precipitates were dried at 110° C. for 16 h followed by calcinations at 500° C. under continuous flow of helium for 24 h. The calcined catalysts were pelleted and sieved (0.65-0.85 mm).

EXAMPLE 5

$Co_{0.177}Mo_{0.547}C$ 100 ml each of Co and Mo solutions was prepared by dissolving 14.7 g of cobalt acetate [$Co(CH_3CO_2)_2$] and 32.2 g of ammonium molybdate tetrahydrate [$(NH_4)_6Mo_7O_{24}\cdot 4H_2O$] in distilled water. Both solutions were premixed and heated to 80° C. The $NH_3$ precipitating solution (200 ml of 5.6M $NH_3$ solution) was also preheated to 80°°. 4 g of activated carbon (derived from coconut shell having a BET surface area of 800 $m^2/g$) was added into 100 ml of distilled water in the precipitation vessel. Both reagents (mixed metal salts solutions and $NH_3$ solution) were combined together in the reaction vessel at 80° C. at a combined pumping rate of 6.7 ml/min (3.3 ml/min $NH_3$ solution, 3.3 ml/min metals solution). The reagents were combined in the reaction vessel (80° C.) containing activated carbon in 100 ml of water. The pH was varied from 4.35-9.00. The duration of reaction was approximately 1 h. This solution was immediately filtered through a preheated funnel and washed (using 500 ml of warm distilled water). The precipitates were dried at 110° C. for 16 h followed by calcinations at 500° C. under continuous flow of helium for 24 h. The calcined catalysts were pelleted and sieved (0.65-0.85 mm).

Catalyst Testing

Catalyst material (0.5 g) were loaded in a reactor and reduced with $H_2$ at 350-400° C. for several hours. Pressure was increased to 75 bar. All catalysts were tested under similar reaction conditions (T=250° C.; p=75 bar; and WHSV=1225 $h^{-1}$). The composition of the feed stream was $CO:H_2:N_2$=47.5:47.5:5. Accordingly, the feedstream comprised syngas having $CO:H_2$ molar ratio of 1.

Analysis of gaseous product was achieved by an online gas chromatograph (GC, Varian 3800). A 5 m*⅛ inch stainless steel Porapak-Q column (mesh size 80-100) was used to separate the reactants and products. Concentrations of hydrogen, carbon monoxide, carbon dioxide and nitrogen were analyzed by a thermal conductivity detector (TCD). The TCD compares the conductivity of the analyzed gas to that of a reference gas. Conversion was determined using an internal standard, nitrogen. Organic compounds such as hydrocarbons and oxygenates were determined by a flame ionization detector (FID). By using a hydrogen and air flame, the FID burns the organic compounds into ions whose amounts are roughly proportional to the number of carbon atoms present. Liquid products from alcohols reactor were collected and identified by gas chromatography mass spectrometer (GC-MS, Perkin Elmer TurboMass). Quantification of liquid products was determined by an offline GC equipped with a Chrompack capillary column (CP-Sil 8CB, 30 m, 0.32 mm, 1 μm) and an FID detector.

The provided values have been calculated as follows:

Conversion:

An indication of the activity of the catalyst was determined by the extent of conversion of the carbon monoxide or for more active catalysts by the extent of volume reduction of the reagent gases (using nitrogen as internal standard). The basic equation used was:

$$\text{Conversion \%} = \text{Moles of } CO_{in} - \text{moles of } CO_{out}/\text{moles of } CO_{in} * 100/1$$

Selectivity

First of all, the varying response of the detector to each product component was converted into % v/v by, multiplying them with online calibration factors. Then these were converted into moles by taking account the flow out of internal standard, moles of feed in and time in hours. Moles of each product were converted into mole-% and selectivity-% was measured by taking carbon numbers into account.

TABLE 1

| | Example | | | | |
|---|---|---|---|---|---|
| | 1 | 2 | 3 | 4 | 5 |
| Catalyst | CoMoS$_2$ | Co$_{0.159}$Mo$_{0.079}$C | Co$_{0.159}$Mo$_{0.079}$C | Co$_{0.126}$Mo$_{0.766}$C | Co$_{0.177}$Mo$_{0.547}$C |
| Co/Mo/C (wt-%) | | 14./47.85/ 37.57 | 14.58/47.85/ 37.57 | 13.92/70.05/ 16.05 | 7.5/79.50/ 12.99 |
| BET surface area (m$^2$/g) | | 400 | 415 | 350 | 340 |
| pH | | 8 | 9 | 9 | 9 |
| Precipitant conc (M) | | 11.6 | 5.6 | 5.6 | 5.6 |
| H$_2$:CO | 1 | 1 | 1 | 1 | 1 |
| CO Conversion (mole-%) | 41 | 23 | 28 | 21 | 17 |
| CO$_2$ | 35.46 | 0.58 | 3.8 | 7.5 | 11.5 |
| CH$_4$ | 9.19 | 2.7 | 1.27 | 12 | 15.3 |
| C$_2$-C$_6$ | 26.89 | 2.45 | 1 | 15.5 | 25 |
| Methanol | 10.6 | 19.68 | 26.21 | 17.5 | 13.5 |
| ethanol | 20.56 | 21.4 | 30.7 | 21 | 16.3 |
| propanol | 21.56 | 24.9 | 33.6 | 22 | 15 |
| 1-butanol | 5.37 | 24.96 | 2 | 2.5 | 1.5 |
| higher alcohols | 9.16 | 3.33 | 3.8 | 2 | 1.9 |
| total ALCOH | 67.26 | 94.27 | 96.31 | 65 | 48.2 |

Table 1 clearly shows that the catalyst of the present invention has a significantly increased selectivity for methanol when compared to a conventional carbon supported cobalt molybdenum catalyst. In addition thereto, a decrease in $CO_2$ formation could be observed, which is an undesired side-products produced in F-T synthesis. The selectivity pattern of alcohols also depends on the pH of precipitation mixture and the concentration of precipitant, wherein the selectivity for methanol, ethanol and propanol is increased in case the pH of the precipitation mixture is increase from 8 to 9.

FIGS. 1 and 2 show XRD pattern of two catalysts prepared at different pH 8 (Example 2) and pH 9 (Example 3). The pH difference and concentration of the precipitant also affects the morphology of catalyst material. The catalyst prepared at pH 8 precipitated with more concentrated solution of ammonium hydroxide was found to be more crystalline and the one prepared at pH 9 with less concentrated solution of ammonium hydroxide showed an amorphous morphology. The XRD data were obtained using standard X-ray diffraction meter at 2 theta value from 1 to 100 within 1 hr.

EXAMPLE 6

Co$_{0.126}$Mo$_{0.255}$C 100 ml each of Co and Mo solutions was prepared by dissolving 10.5 g of cobalt acetate [Co(CH$_3$CO$_2$)$_2$] and 15 g of ammonium molybdate tetrahydrate [(NH$_4$)$_6$Mo$_7$O$_{24}$.4H$_2$O] in distilled water. Both solutions were premixed and heated to 80° C. The NH3 precipitating solution (200 ml of 5.6M NH$_3$ solution) was also preheated to 80° C. 4 g of activated carbon (derived from coconut shell having a BET surface area of 800 m$^2$/g) was added into 100 ml of distilled water in the precipitation vessel. Both reagents (mixed metal salts solutions and NH$_3$ solution) were combined together in the reaction vessel at 80° C. at a combined pumping rate of 6.7 ml/min (3.3 ml/min NH$_3$ solution, 3.3 ml/min metals solution). The reagents were combined in the reaction vessel (80° C.) containing activated carbon in 100 ml of water. The pH was varied from 4.35-9.00. The duration of reaction was ca. 1 h. This solution was filtered and washed. The precipitates were dried at 110° C. for 16 h followed by thermal cooking and activation of catalyst at 400° C. under continuous flow of helium/nitrogen for 12 to 24 hrs and used for syngas conversion.

EXAMPLE 7

Co$_{0.126}$Mo$_{0.255}$C 100 ml each of Co and Mo solutions was prepared by dissolving 10.5 g of cobalt acetate [Co(CH$_3$CO$_2$)$_2$] and 15 g of ammonium molybdate tetrahydrate [(NH$_4$)$_6$Mo$_7$O$_{24}$.4H$_2$O] in distilled water. Both solutions were premixed and heated to 80° C. The NH3 precipitating solution (200 ml of 5.6M NH$_3$ solution) was also preheated to 80° C. 4 g of activated carbon (derived from coconut shell having a BET surface area of 800 m$^2$/g) was added into 100 ml of distilled water in the precipitation vessel. Both reagents (mixed metal salts solutions and NH$_3$ solution) were combined together in the reaction vessel at 80° C. at a combined pumping rate of 6.7 ml/min (3.3 ml/min NH$_3$ solution, 3.3 ml/min metals solution). The reagents were combined in the reaction vessel (80° C.) containing activated carbon in 100 ml of water. The pH was varied from 4.35-9.00. The duration of reaction was ca. 1 h. This solution was filtered and washed. The precipitates were dried at 110° C. for 16 h followed by thermal cooking and activation of catalyst at 500° C. under continuous flow of helium/nitrogen for 12 to 24 hrs and used for syngas conversion.

EXAMPLE 8 (COMPARATIVE EXAMPLE—WO 2010/002618 A1)

Co$_{0.126}$Mo$_{0.255}$C 100 ml each of Co and Mo solutions was prepared by dissolving 10.5 g of cobalt acetate [Co(CH$_3$CO$_2$)$_2$] and 15 g of ammonium molybdate tetrahydrate [(NH$_4$)$_6$Mo$_7$O$_{24}$.4H$_2$O] in distilled water. Both solutions were premixed and heated to 80° C. The NH3 precipitating solution (200 ml of 5.6M NH$_3$ solution) was also preheated to 80° C. 4 g of activated carbon (derived from coconut shell having a BET surface area of 800 m$^2$/g) was added into 100 ml of distilled water in the precipitation vessel. Both reagents (mixed metal salts solutions and NH$_3$ solution) were combined together in the reaction vessel at 80° C. at a combined pumping rate of 6.7 ml/min (3.3 ml/min NH$_3$ solution, 3.3 ml/min metals solution). The reagents were combined in the reaction vessel (80° C.) containing activated carbon in 100 ml of water. The pH was varied from 4.35-9.00. The duration of reaction was ca. 1 h. This solution was filtered and washed. The precipitates were dried at 110° C. for 16 h followed by thermal cooking and activation of catalyst at 600° C. under continuous flow of helium/nitrogen for 12 to 24 hrs and used for syngas conversion.

EXAMPLE 9 (COMPARATIVE EXAMPLE—WO 2010/002618 A1)

$Co_{0.126}Mo_{0.255}C$ 100 ml each of Co and Mo solutions was prepared by dissolving 10.5 g of cobalt acetate [Co(CH$_3$CO$_2$)$_2$] and 15 g of ammonium molybdate tetrahydrate [(NH$_4$)$_6$Mo$_7$O$_{24}$.4H$_2$O] in distilled water. Both solutions were premixed and heated to 80° C. The NH3 precipitating solution (200 ml of 5.6M NH$_3$ solution) was also preheated to 80° C. 4 g of activated carbon (derived from coconut shell having a BET surface area of 800 m$^2$/g) was added into 100 ml of distilled water in the precipitation vessel. Both reagents (mixed metal salts solutions and NH$_3$ solution) were combined together in the reaction vessel at 80° C. at a combined pumping rate of 6.7 ml/min (3.3 ml/min NH$_3$ solution, 3.3 ml/min metals solution). The reagents were combined in the reaction vessel (80° C.) containing activated carbon in 100 ml of water. The pH was varied from 4.35-9.00. The duration of reaction was ca. 1 h. This solution was filtered and washed. The precipitates were dried at 110° C. for 16 h followed by thermal cooking and activation of catalyst at 700° C. under continuous flow of helium/nitrogen for 12 to 24 hrs and used for syngas conversion.

EXAMPLE 10 (COMPARATIVE EXAMPLE—WO 2010/002618 A1)

$Co_{0.126}Mo_{0.255}C$ 100 ml each of Co and Mo solutions was prepared by dissolving 10.5 g of cobalt acetate [Co(CH$_3$CO$_2$)$_2$] and 15 g of ammonium molybdate tetrahydrate [(NH$_4$)$_6$Mo$_7$O$_{24}$.4H$_2$O] in distilled water. Both solutions were premixed and heated to 80° C. The NH3 precipitating solution (200 ml of 5.6M NH$_3$ solution) was also preheated to 80° C. 4 g of activated carbon (derived from coconut shell) was added into 100 ml of distilled water in the precipitation vessel. Both reagents (mixed metal salts solutions and NH$_3$ solution) were combined together in the reaction vessel at 80° C. at a combined pumping rate of 6.7 ml/min (3.3 ml/min NH$_3$ solution, 3.3 ml/min metals solution). The reagents were combined in the reaction vessel (80° C.) containing activated carbon in 100 ml of water. The pH was varied from 4.35-9.00. The duration of reaction was ca. 1 h. This solution was filtered and washed. The precipitates were dried at 110° C. for 16 h followed by thermal cooking and activation of catalyst at 800° C. under continuous flow of helium/nitrogen for 12 to 24 hrs and used for syngas conversion.

Catalyst Testing

The comparative catalysts were tested under similar reaction conditions as the catalysts according to the present invention (T=250° C.; p=75 bar; and WHSV=1225 h$^{-1}$). The composition of the feedstream was CO:H$_2$:N$_2$=47.5:47.5:5. Accordingly, the feedstream comprised syngas having CO:H$_2$ molar ratio of 1.

TABLE 2

| | Example | | | | |
|---|---|---|---|---|---|
| | 6 | 7 | 8 | 9 | 10 |
| Catalyst | $Co_{0.126}Mo_{0.255}C$ | $Co_{0.126}Mo_{0.255}C$ | $Co_{0.126}Mo_{0.255}C$ | $Co_{0.126}Mo_{0.255}C$ | $Co_{0.126}Mo_{0.255}C$ |
| Co/Mo/C (wt-%) | 15.88/56.42/ 27.69 | 15.88/56.42/ 27.69 | 15.88/56.42/ 27.69 | 15.88/56.42/ 27.69 | 15.88/56.42/ 27.69 |
| pH | 9 | 9 | 9 | 9 | 9 |
| Precipitant conc (M) | 5.6 | 5.6 | 5.6 | 5.6 | 5.6 |
| H$_2$:CO | 1 | 1 | 1 | 1 | 1 |
| BET (m$^2$/g) | 366 | 351 | 311 | 267 | 210 |
| CO Conversion (mole-%) | 39.8 | 36.5 | 24.3 | 19 | 11 |
| CO$_2$ | 5 | 8.3 | 11.5 | 21.6 | 35 |
| CH$_4$ | 15.5 | 11 | 5.2 | 5.4 | 2.3 |
| C$_2$-C$_6$ | 21 | 13 | 32 | 36 | 41 |
| Methanol | 21 | 18.5 | 19 | 19.7 | 11.2 |
| ethanol | 25.3 | 30.1 | 22 | 9.6 | 5.4 |
| propanol | 9 | 16.6 | 9.1 | 4.5 | 5.1 |
| 1-butanol | 3.2 | 2.5 | 1.2 | 3.2 | 0 |
| total alcohols | 59.1 | 67.7 | 51.3 | 37 | 21.7 |

Table 2 clearly shows that the catalyst of the present invention has a dramatically improved CO conversion in combination with a significantly increased selectivity for alcohols when compared to a carbon supported carbon supported cobalt molybdenum catalyst having a lower BET surface area, like the catalyst suggested in WO 2010/002618 A1. Moreover, it is evident from Table 2 that a lower calcination temperature is to be selected when preparing the carbon supported cobalt molybdenum catalyst.

The invention claimed is:
1. A catalyst composition consisting of cobalt (Co); molybdenum (Mo); and optionally an alkali metal or an alkaline earth metal on an activated carbon support (C)

wherein the relative molar ratios of the elements in said composition are of the following formula:

$Co_aMo_bM_cC$ wherein:
M is one or more elements selected from the group consisting of alkali metal and alkaline earth metal;
a is 1E-3-0.3;
b is 1E-3-0.9;
c is 0-1E-2; and
wherein said Co and Mo are in their metallic form and wherein the catalyst composition has a BET surface area of at least 320 m$^2$/g.

2. The catalyst composition according to claim 1, wherein M is selected from the group consisting of potassium (K), sodium (Na), calcium (Ca) and magnesium (Mg).

3. The catalyst composition according to claim 1, wherein:
a is 1E-2-0.3; and
b is 5E-3-0.9.

4. The catalyst composition according to claim 1, wherein the catalyst composition has a BET surface area of 350-1200 m$^2$/g.

5. The catalyst composition according to claim 1, wherein the Co and/or Mo are not in sulphide form.

6. The catalyst composition according to claim 1, wherein said catalyst composition further comprises an inert binder.

* * * * *